(12) United States Patent
Taylor

(10) Patent No.: US 6,544,485 B1
(45) Date of Patent: *Apr. 8, 2003

(54) ELECTRO-KINETIC DEVICE WITH ENHANCED ANTI-MICROORGANISM CAPABILITY

(75) Inventor: Charles E. Taylor, Sebastopol, CA (US)

(73) Assignee: Sharper Image Corporation, San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/774,198

(22) Filed: Jan. 29, 2001

(51) Int. Cl.$^7$ ................................................ B01J 19/08
(52) U.S. Cl. ........................... 422/186.04; 422/186.12; 422/186.3; 422/121
(58) Field of Search .................... 422/121, 186.04, 422/186.3, 186.12

(56) References Cited

U.S. PATENT DOCUMENTS

| | | | |
|---|---|---|---|
| 2,327,588 A | 8/1943 | Bennett | 315/326 |
| 2,590,447 A | 3/1952 | Nord, Jr. et al. | 128/393 |
| 2,949,550 A | 8/1960 | Brown | 310/5 |
| 3,793,744 A | 2/1974 | Saita | 34/104 |
| 3,910,778 A | 10/1975 | Shahgholi et al. | 55/102 |
| 3,981,695 A | 9/1976 | Fuchs | 55/138 |
| 3,984,215 A | 10/1976 | Zucker | 55/2 |
| 4,052,177 A | 10/1977 | Kide | 55/139 |
| 4,102,654 A | 7/1978 | Pellin | 55/102 |
| 4,138,233 A | 2/1979 | Masuda | 55/139 |
| 4,209,306 A | 6/1980 | Feldman et al. | 55/2 |
| 4,227,894 A | 10/1980 | Proynoff | 96/58 |
| 4,231,766 A | 11/1980 | Spurgin | 55/138 |
| 4,232,355 A | 11/1980 | Finger et al. | 361/235 |
| 4,244,712 A | 1/1981 | Tongret | 55/124 |
| 4,259,452 A | 3/1981 | Yukuta et al. | 521/52 |

(List continued on next page.)

FOREIGN PATENT DOCUMENTS

| | | |
|---|---|---|
| FR | 2690509 | 10/1993 |
| JP | 10137007 | 5/1998 |
| JP | 11104223 | 4/1999 |
| JP | 2000236914 | 9/2000 |
| WO | WO 01/47803 A1 | 7/2001 |
| WO | WO 01/48781 A1 | 7/2001 |

OTHER PUBLICATIONS

U.S. patent application Ser. No. 09/197,131, Taylor et al., filed Nov. 20, 1998.

U.S. patent application Ser. No. 09/249,375, Taylor et al., filed Feb. 12, 1999.

"Zenion Elf Device", drawing, prior art.

Electrical Schematic and promotional material available from Zenion Industries, 7 pages, Aug. 1990.

Promotional material available from Zenion Industries for the Plasma–Pure 100/200/300, 2 pages, Aug. 1990.

(List continued on next page.)

*Primary Examiner*—Kishor Mayekar
(74) *Attorney, Agent, or Firm*—Fliesler, Dubb Meyer & Lovejoy LLP

(57) ABSTRACT

An electronic device generates an output airflow that is subjected to UV radiation from a germicidal lamp within the device. The airflow preferably is created electro-kinetically by coupling high voltage pulses across an electrode system that includes small radius first array electrodes and larger radius second array electrodes. The airflow is also accompanied by generation of ions and/or ozone. If desired, airflow may be created with a fan instead of, or to augment, electro-kinetic generation. The device optionally includes a moisture-containing material whose proximity to the airflow can augment humidity in the airflow.

37 Claims, 5 Drawing Sheets

U.S. PATENT DOCUMENTS

| | | | | |
|---|---|---|---|---|
| 4,266,948 | A | 5/1981 | Teague et al. | 55/126 |
| 4,282,014 | A | 8/1981 | Winkler et al. | 55/105 |
| 4,342,571 | A | 8/1982 | Hayashi | 55/137 |
| 4,386,395 | A | 5/1983 | Francis, Jr. | 363/27 |
| 4,413,225 | A | 11/1983 | Donig et al. | 323/246 |
| 4,445,911 | A | 5/1984 | Lind | 55/2 |
| 4,477,263 | A | 10/1984 | Shaver et al. | 95/7 |
| 4,496,375 | A | 1/1985 | Le Vantine | 96/66 |
| 4,502,002 | A | 2/1985 | Ando | 323/237 |
| 4,536,698 | A | 8/1985 | Shevalenko et al. | 323/237 |
| 4,587,475 | A | 5/1986 | Finney, Jr. et al. | 323/241 |
| 4,600,411 | A | 7/1986 | Santamaria | 55/139 |
| 4,601,733 | A | 7/1986 | Ordines et al. | 55/139 |
| 4,626,261 | A | 12/1986 | Jorgensen | 55/2 |
| 4,643,745 | A | 2/1987 | Sakakibara et al. | 96/76 |
| 4,659,342 | A | 4/1987 | Lind | 55/2 |
| 4,674,003 | A | 6/1987 | Zylka | 361/235 |
| 4,694,376 | A | 9/1987 | Gesslauer | 361/235 |
| 4,713,093 | A | 12/1987 | Hansson | 55/139 |
| 4,713,724 | A | 12/1987 | Voelkel | 361/231 |
| 4,750,917 | A | 6/1988 | Fujii | 55/6 |
| 4,779,182 | A | 10/1988 | Mickal et al. | 363/37 |
| 4,789,801 | A | 12/1988 | Lee | 310/308 |
| 4,798,338 | A | 1/1989 | Bauch et al. | 239/692 |
| 4,808,200 | A | 2/1989 | Dallhammer et al. | 55/105 |
| 4,811,159 | A | 3/1989 | Foster, Jr. | 361/231 |
| 4,940,470 | A | 7/1990 | Jaisinghani et al. | 55/2 |
| 4,941,068 | A | 7/1990 | Hofmann | 361/231 |
| 5,010,869 | A | 4/1991 | Lee | 123/539 |
| 5,024,685 | A | 6/1991 | Torok et al. | 96/43 |
| 5,141,529 | A | 8/1992 | Oakley et al. | 95/57 |
| 5,185,015 | A | 2/1993 | Searle | 55/102 |
| 5,196,171 | A | 3/1993 | Peltier | 422/121 |
| 5,215,558 | A | 6/1993 | Moon | 96/62 |
| 5,217,504 | A | 6/1993 | Johansson | 55/2 |
| 5,302,190 | A | 4/1994 | Williams | 95/57 |
| 5,315,838 | A | 5/1994 | Thompson | 62/129 |
| 5,316,741 | A | 5/1994 | Sewell et al. | 422/186.21 |
| 5,330,722 | A | 7/1994 | Pick et al. | 422/121 |
| 5,378,978 | A | 1/1995 | Gallo et al. | 323/241 |
| 5,484,472 | A | 1/1996 | Weinberg | 96/26 |
| 5,492,557 | A | 2/1996 | Vanella | 96/16 |
| 5,535,089 | A | 7/1996 | Ford et al. | 361/231 |
| 5,578,112 | A | 11/1996 | Krause | 96/24 |
| 5,601,636 | A | 2/1997 | Glucksman | 96/63 |
| 5,601,786 | A | * 2/1997 | Monagan | 422/121 |
| 5,656,063 | A | 8/1997 | Hsu | 95/58 |
| 5,667,564 | A | 9/1997 | Weinberg | 96/58 |
| 5,702,507 | A | 12/1997 | Wang | 96/55 |
| 5,755,103 | A | 5/1998 | Na et al. | 62/78 |
| 5,779,769 | A | 7/1998 | Jiang | 96/55 |
| 5,814,135 | A | 9/1998 | Weinberg | 96/58 |
| 5,879,435 | A | 3/1999 | Satyapal et al. | 96/16 |
| 5,893,977 | A | 4/1999 | Pucci | 210/739 |
| 5,911,957 | A | 6/1999 | Khatchatrian et al. | 422/186.07 |
| 5,972,076 | A | 10/1999 | Nichols et al. | 95/81 |
| 5,975,090 | A | 11/1999 | Taylor et al. | 132/116 |
| 5,993,738 | A | 11/1999 | Goswani | 422/22 |
| 6,019,815 | A | 2/2000 | Satyapal et al. | 95/74 |
| 6,042,637 | A | 3/2000 | Weinberg | 96/58 |
| 6,063,168 | A | 5/2000 | Nichols et al. | 96/80 |
| 6,086,657 | A | 7/2000 | Freije | 95/2 |
| 6,126,722 | A | 10/2000 | Mitchell et al. | 95/57 |
| 6,149,717 | A | 11/2000 | Satyapal et al. | 96/16 |
| 6,149,815 | A | 11/2000 | Sauter | 210/635 |
| 6,152,146 | A | 11/2000 | Taylor et al. | 132/116 |
| 6,163,098 | A | 12/2000 | Taylor et al. | 310/308 |
| 6,176,977 | B1 | 1/2001 | Taylor et al. | 204/176 |
| 6,182,461 | B1 | 2/2001 | Washburn et al. | 62/264 |
| 6,182,671 | B1 | 2/2001 | Taylor et al. | 132/116 |
| 6,193,852 | B1 | 2/2001 | Caracciolo et al. | 204/176 |
| 6,212,883 | B1 | 4/2001 | Kang | 60/275 |
| 6,252,012 | B1 | 6/2001 | Egitto et al. | 525/431 |
| 6,270,733 | B1 | 8/2001 | Rodden | 422/186.07 |
| 6,277,248 | B1 | 8/2001 | Ishioka et al. | 204/176 |
| D449,097 | S | 10/2001 | Smith et al. | D23/364 |
| D449,679 | S | 10/2001 | Smith et al. | D23/365 |
| 6,302,944 | B1 | 10/2001 | Hoenig | 96/16 |
| 6,309,514 | B1 | 10/2001 | Conrad et al. | 204/164 |
| 6,312,507 | B1 | 11/2001 | Taylor et al. | 96/19 |
| 6,315,821 | B1 | 11/2001 | Pillion et al. | 96/416 |
| 6,328,791 | B1 | 12/2001 | Pillion et al. | 96/418 |
| 6,350,417 | B1 | 2/2002 | Lau et al. | 422/186.04 |
| 6,372,097 | B1 | 4/2002 | Chen | 204/176 |
| 6,379,427 | B1 | 4/2002 | Siess | 95/57 |
| 6,391,259 | B1 | 5/2002 | Malkin et al. | 422/28 |

OTHER PUBLICATIONS

Promotional material available from Zenion Industries for the Plasma–Tron, 2 pages, Aug. 1990.

U.S. patent application Ser. No. 09/669,253, Taylor et al., filed Sep. 25, 2000.

U.S. patent application Ser. No. 09/669,268, Taylor et al., filed Sep. 25, 2000.

U.S. patent application Ser. No. 09/730,499, Taylor et al., filed Dec. 5, 2000.

U.S. patent application Ser. No. 09/742,814, Taylor et al., filed Dec. 19, 2000.

U.S. patent application Ser. No. 09/774,198, Taylor, filed Jan. 29, 2001.

U.S. patent application Ser. No. 09/924,600, Taylor et al., filed Aug. 8, 2001.

U.S. patent application Ser. No. 10/023,197, Taylor et al., filed Dec. 13, 2001.

U.S. patent application Ser. No. 10/023,460, Taylor et al., filed Dec. 13, 2001.

U.S. patent application Ser. No. 10/074,082, Taylor et al., filed Feb. 12, 2002.

U.S. patent application Ser. No. 10/074,096, Taylor et al., filed Feb. 12, 2002.

U.S. patent application Ser. No. 10/074,103, Sinaiko et al., filed Feb. 12, 2000.

U.S. patent application Ser. No. 10/074,207, Taylor et al., filed Feb. 12, 2002.

U.S. patent application Ser. No. 10/074,208, Taylor., filed Feb. 12, 2002.

U.S. paten application Ser. No. 10/074,209, Taylor et al., filed Feb. 12, 2002.

U.S. patent application Ser. No. 10/074,339, Taylor et al., filed Feb. 12, 2002.

U.S. patent application Ser. No. 10/074,347, Taylor et al., Feb. 12, 2002.

U.S. patent application Ser. No. 10/074,379, Taylor et al., filed Feb. 12, 2002.

U.S. patent application Ser. No. 10/074,549, Sinaiko et al., filed Feb. 12, 2002.

U.S. patent application Ser. No. 10/074,827, McKinney, Jr. et al., filed Feb. 12, 2002.

U.S. patent application Ser. No. 10/156,158, Taylor et al., filed May 28, 2002.

U.S. patent application Ser. No. 10/188,668, Taylor et al., filed Jul. 2, 2002.

Lentek Sila ™ Plug–In Air Purifier/Deodorizer product box copyrighted 1999.

* cited by examiner

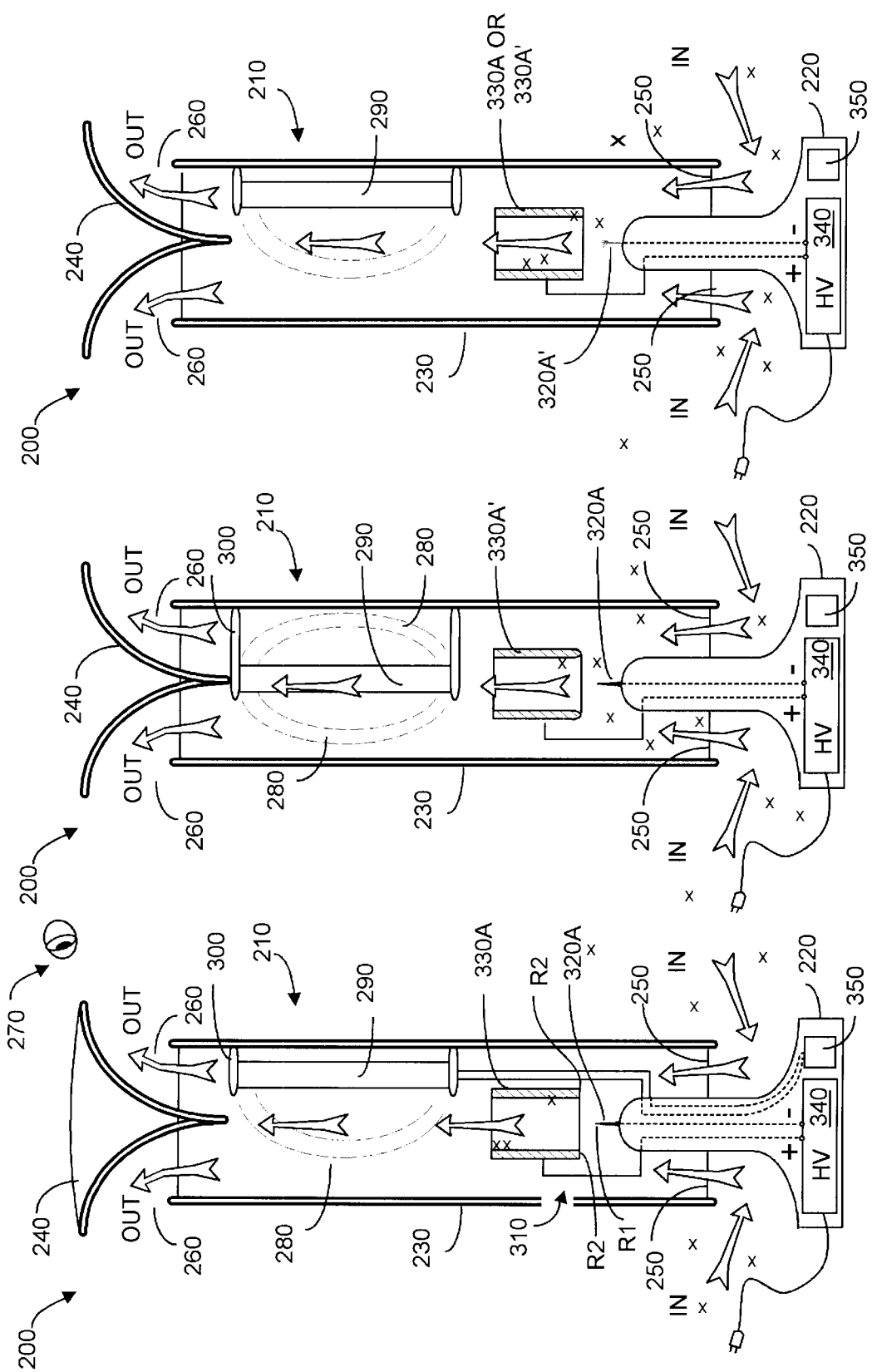

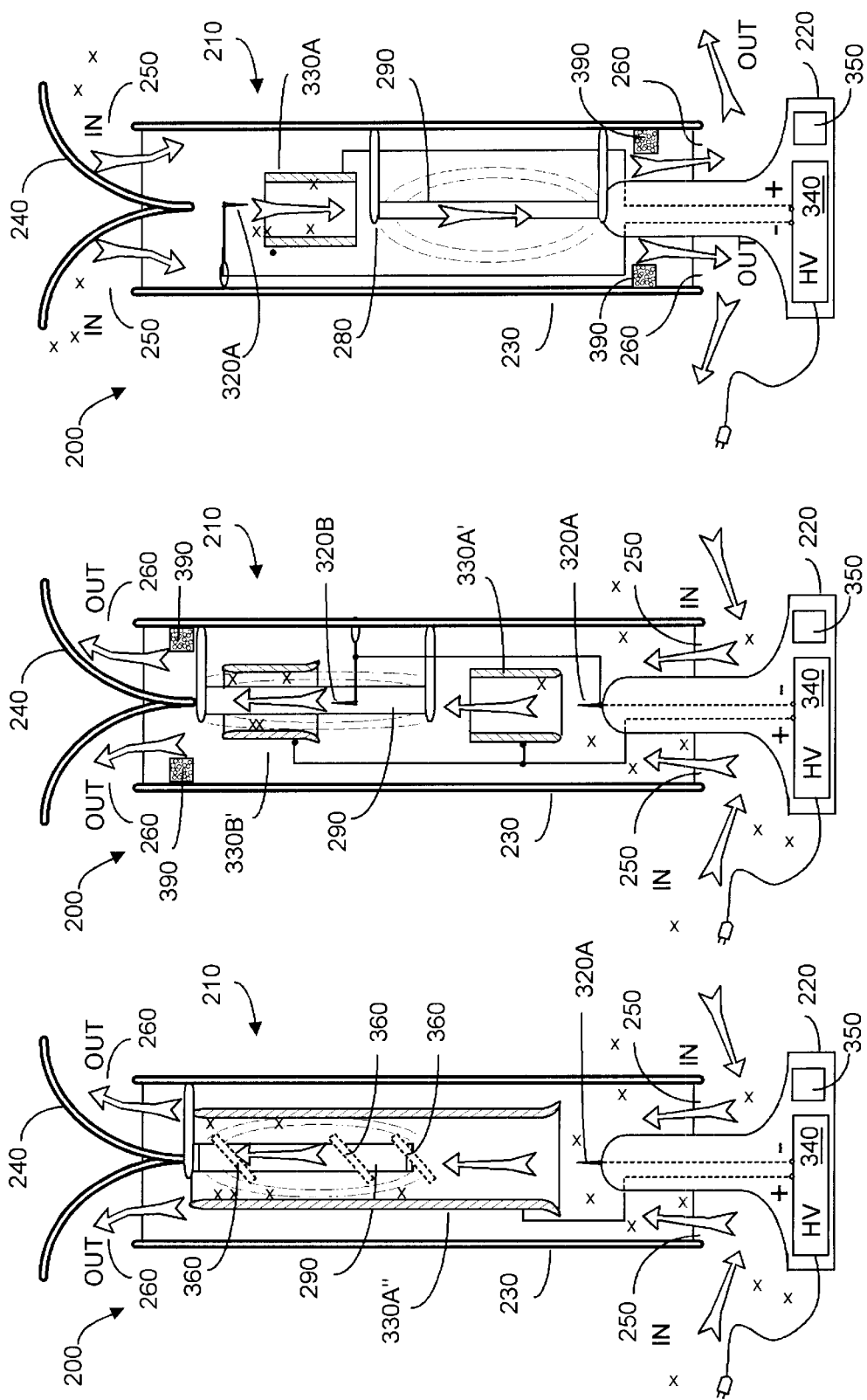

ELECTRO-KINETIC DEVICE WITH ENHANCED ANTI-MICROORGANISM CAPABILITY

FIELD OF THE INVENTION

The present invention relates generally to devices that can condition the air in a room, including so-called electro-kinetic devices that output ionized air, typically accompanied by ozone ($O_3$), and more specifically to providing such devices with enhanced ability to kill microorganisms, including germs, bacteria, and viruses in the room environment.

BACKGROUND OF THE INVENTION

U.S. Pat. No. 6,163,098 to Taylor et al. and U.S. Pat. No. 4,789,801 to Lee describe various devices to generate a stream of ionized air using so-called electro-kinetic techniques. In some applications, the electro-kinetic devices may be small enough to be handheld, and in other applications electro-kinetic devices may be large enough to condition the air in a room. In overview, electro-kinetic techniques use high electric fields to ionize air molecules, a process that produces ozone ($O_3$) as a byproduct. Ozone is an unstable molecule of oxygen that is commonly produced as a byproduct of high voltage arcing. In safe concentrations, ozone can be a desirable and useful substance. But ozone by itself may not be effective to kill microorganisms such as germs, bacteria, and viruses in the environment surrounding the device.

FIG. 1 depicts a generic electro-kinetic device 10 to generate ozone. Device 10 includes a housing 20 that typically has at least one air input port 30 and at least one air output port 40. Within housing 20 there is disposed an electrode assembly or system 50 comprising a first electrode array 60 having at least one electrode 70 and comprising a second electrode array 80 having at least one electrode 90. System 10 further includes a high voltage generator 100 coupled between the first and second electrode arrays. Electrodes 70 and electrodes 90 may have a variety of shapes. For example, electrodes 70 may be thin electrical wires, and electrodes 90 may be larger wires, rods, or other shapes. Electrodes 70 may be pointed or pin-like, and electrodes 90 may be curvilinear, including ring shaped, or may comprise a conductive plate with curved or ring-like openings formed in the plate. Electrodes 90 typically are symmetrically disposed relative to electrodes 70. For example, if there are three electrodes 70 in first electrode array 60, there might be two electrodes 90 in second electrode array 80, wherein electrodes 90 are staggered to be equidistant from the nearest electrodes 70. In the pin and ring type configurations, electrodes 90 are preferably concentric with electrodes 70.

In the various configurations, all of the electrodes are electrically conductive material, metal for example. Electrodes 90 preferably have a larger radius than electrodes 70, with the result that a large electric field is created at or adjacent electrodes 90 upon application of high voltage (typically several kV) from generator 100. As a result, ozone and ionized particles of air are generated within device 10, and there is an electro-kinetic flow of air in the direction from the first electrode array 60 towards the second electrode array 80. In FIG. 1, the large arrow denoted IN represents ambient air that can enter input port 30. The small "x's" denote particulate matter that may be present in the incoming ambient air. The air movement is in the direction of the large arrows, and the output airflow, denoted OUT, exits device 10 via port 40. An advantage of electro-kinetic devices such as device 10 is that an air flow is created without using fans or other moving parts to create the air flow.

Preferably particulate matter x in the ambient air can be electrostatically attracted to the second electrode array 80, with the result that the outflow (OUT) of air from device 10 not only contains ozone and ionized air, but can be cleaner than the ambient air. In such devices, it can become necessary to occasionally clean the second electrode array electrodes 80 to remove particulate matter and other debris from the surface of electrodes 90. Thus, device 10 in FIG. 1 can function somewhat as a fan to create an output air flow, but without requiring moving parts. Ideally the outflow of air (OUT) is conditioned in that particulate matter is removed and the outflow includes safe amounts of ozone, and some ions.

But an outflow of air containing ions and ozone may not destroy or reduce microorganisms such as germs, bacteria, fungi, viruses, and the like, collectively hereinafter "microorganisms". It is known in the art to try to destroy such microorganisms with so-called germicidal lamps. Such lamps emit ultra violet radiation having a wavelength of about 254 nm. For example, devices to condition air using mechanical fans, HEPA filters, and germicidal lamps are sold commercially by companies such as Austin Air, C.A.R.E. 2000, Amaircare, and others. Often the devices are somewhat cumbersome, and have size and bulk of a small filing cabinet. In such devices, care must be taken to ensure that ultraviolet radiation from the germicidal lamp cannot be viewed by nearby persons, to prevent eye injury. Although such fan-powered devices can reduce or destroy microorganisms, the devices tend to be bulky, and are not necessarily silent in operation.

What is needed is a device to condition air in a room that can operate relatively silently to remove particulate matter in the air, that can preferably output safe amounts of ozone, and that can also kill or reduce microorganisms such as germs, fungi, bacteria, viruses, and the like.

The present invention provides such a device.

SUMMARY OF THE PRESENT INVENTION

In a first aspect, the invention provides an electro-kinetic ionizing device with a baffle mechanism and a germicidal lamp housed within the device such that the baffle mechanism precludes lamp ultraviolet radiation from being viewed by humans. In one configuration, the germicidal lamp is disposed vertically within a somewhat tubular housing, with an array of first and second electrodes disposed axially at one lamp end. In an alternative embodiment, there is an array of first and second electrodes disposed axially at each lamp end. In the various embodiments, intake and outlet vents at each end of the housing promote flow of electro-kinetically moved air without permitting viewing of the lamp radiation.

Preferred electrode array configurations include pin-ring and elongated pin-ring electrodes, including pin electrodes formed from an arc or ring of tapered conductive material, and symmetrically disposed arrays of electrodes formed as a single component. The electrodes in an array preferably are symmetrically disposed with respect to each other, and like in the air flow path. Efficacy of the germicidal lamp in destroying bacterial, virus, germs, etc. in the air flow appears to be proportional to the length of time the airflow is subjected to radiation from the lamp. Thus the preferred embodiments of the invention dispose the longitudinal axis of the germicidal lamp parallel to the long axis of the electro-kinetic device.

If desired, moisture containing material such as Porex may be included to augment moisture content in the outflow of conditioned air. In one embodiment, a personal-sized portable device is provided that includes electro-kinetically generated airflow with ions and ozone in the output, reduced particulate matter in the output airflow, and with reduced or eliminated microorganisms as a result of ultraviolet radiation generated from a germicidal type lamp within the device. In an alternative embodiment, the electro-kinetic components may be replaced by a small battery operated fan, to yield a personal device that outputs air substantially devoid of microorganisms. A Porex type element may also be included to allow a user to augment moisture content in the air outflow.

Other features and advantages of the invention will appear from the following description in which the preferred embodiments have been set forth in detail, in conjunction with the accompanying drawings.

BRIEF DESCRIPTION OF THE FIGURES

FIGS. 2A–2F depict embodiments of electro-kinetic conditioner devices with enhanced ability to diminish, inhibit, or destroy microorganisms such as germs, bacteria, and viruses, according to the present invention;

DETAILED DESCRIPTION OF THE PREFERRED EMBODIMENT

Figure 1:
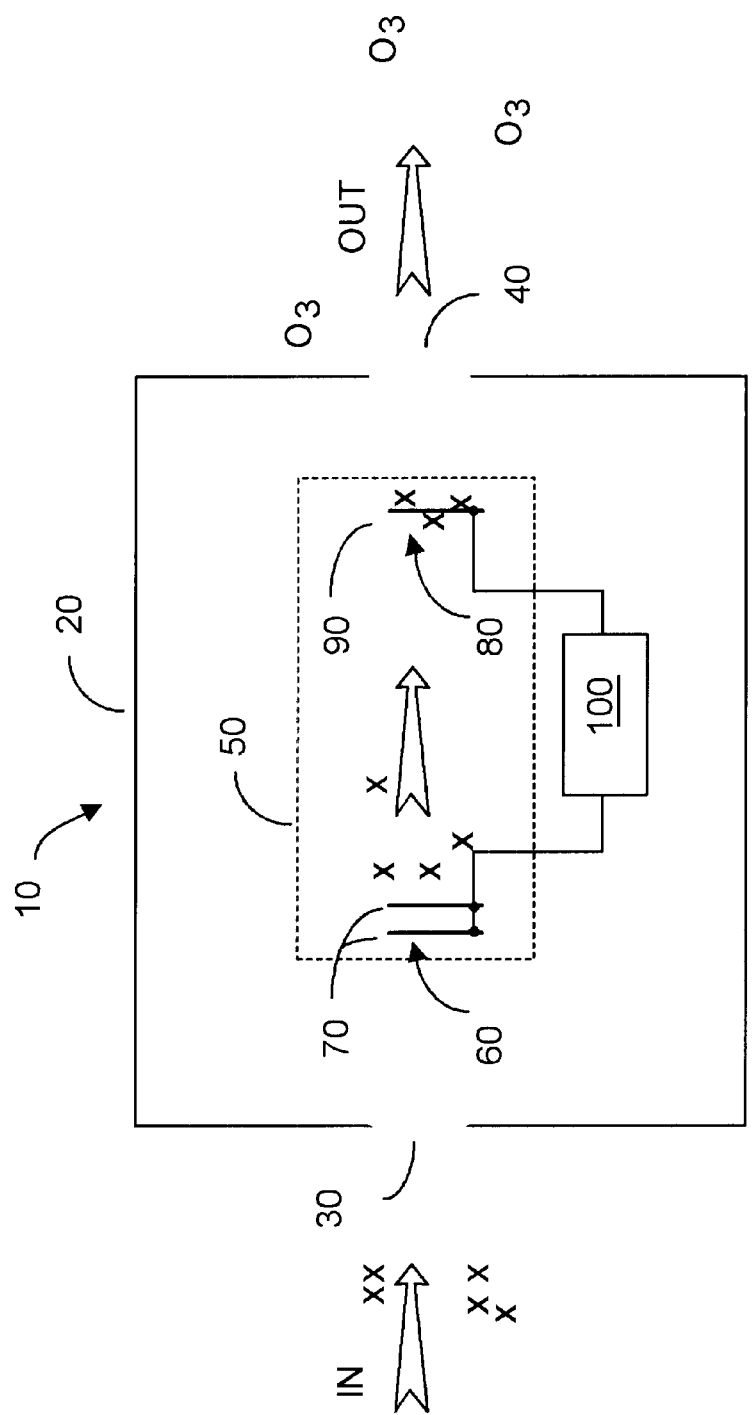
FIG. 1 depicts a generic electro-kinetic conditioner device that outputs ionized air and ozone, according to the prior art.

FIG. 2A depicts a first embodiment of a device 200 that provides electro-kinetic conditioning of ambient air, with improved ability to diminish or destroy microorganisms including bacteria, germs, and viruses. As will now be described, device 200 takes ambient air (IN) that may include such microorganisms, as well as particulate matter (depicted as x). Further, without using moving components, device 10 outputs conditioned air (OUT) that has at least some particulate matter removed, that includes ions, safe amounts of ozone, and is freer of such microorganisms.

Device 200 includes a housing 210 that comprises a base portion 220, a main portion 230, and an upper portion 240 that also serves as a light baffle. Housing 210 includes at least one ambient air intake vent 250, and at least one conditioned air outlet vent 260. As used herein, it will be understood that intake vent 250 is "upstream" relative to outlet vent 260, or that outlet vent 260 is "downstream" from intake vent 250. "Upstream" and "downstream" describe the general flow of air into, through, and out of device 200, as indicated by the large hollow arrows.

One role of housing 210 is to prevent a nearby human, shown as 270, from viewing preferably ultraviolet (UV) radiations or emanations 280 generated by a UV lamp 290 disposed within the housing. UV lamp 290 is a so-called UV-C lamp that preferably emits radiation having wavelength of about 254 nm, which wavelength is effective in diminishing or destroying bacteria, germs, and viruses to which it is exposed. Lamps 290 are commercially available, for example the Phillips model TUO 25W/G25 T8, a 25 W tubular lamp measuring about 25 mm in diameter by about 43 cm in length. Another suitable lamp is the Phillips TUO 8WG8 T6, an 8 W lamp measuring about 15 mm in diameter by about 29 cm in length. Other lamps that emit the desired wavelength may instead be used.

The efficacy of radiation 280 upon microorganism depends upon the length of time such organisms are subjected to the radiation. Thus in the preferred embodiments, lamp 290 is disposed within housing 210 such that the longitudinal axis of the lamp is parallel to the upstream-to-downstream airflow within the housing.

In the configuration of FIG. 2A, lamp 210 is disposed parallel to but not coaxially with the airstream that is created preferably electro-kinetically within device 200. An electro-kinetic airflow is created in the following fashion. Electrode assembly 310 comprises a first electrode array 320A and a second electrode array 330A. In the embodiment of FIG. 2A, array 320A comprises a single pin-type electrically conductive electrode that preferably terminates in a point. In FIG. 2A, array 330A comprises a ring-like electrode that may be constructed from an electrically conductive cylinder. Preferably the edges of this electrode facing electrode 320A are somewhat rounded such that the effective radius R2 of these edges is much larger than the effective radius R1 of electrode 320A. The ratio R2:R1 should be at least ten, and preferably fifteen or more.

A high voltage pulse generator 340 is coupled between electrodes in the first electrode array 320A and electrodes in the second electrode array 330A. Generator 340A receives low input voltage, e.g., 115 VAC to 230 VAC or in some embodiments battery-supplied 6 VDC to 12 VDC and generates high voltage pulses of at least 10 KV peak-to-peak with a repetition rate of about 20 KHz. The pulse train output preferably has a duty cycle of perhaps 10%, especially in battery-operated embodiments, but may have other duty cycles including 100% duty cycle. High voltage pulse generator 340 may be implemented in many ways, and typically will comprise a low voltage oscillator operating at perhaps 20 KHz frequency that outputs low voltage pulses to an electronic switch such as a thyristor. The thyristor or other switch couples the low voltage pulses to the input winding of a step-up transformer whose secondary winding is coupled to a high voltage multiplier circuit outputting the high voltage pulses. The various circuits and components comprising high voltage pulse generator 340 may be fabricated on a printed circuit board mounted within housing 210, for example in the housing base portion 220.

As shown in FIG. 2A, device 200 may include additional circuitry 350, for example a voltage conditioner to provide proper operating voltage for lamp (or lamps) 290, a circuit to allow device 200 to function for a certain amount of time, etc.

In the embodiment of FIG. 2A, the positive output terminal of generator 340 is coupled to the second electrode array 330A, and the negative output terminal is coupled to the first electrode array 320A. This coupling polarity has been found to work well, including minimizing unwanted audible electrode vibration or hum. However the opposite polarity could instead be used, e.g., negative port of generator 340 coupled to electrode(s) 330A and positive port coupled to electrode(s) 320A. As noted, the geometry of electrode(s) 320A is such that at least one relatively narrow or sharp point terminus exists. As one consequence, when voltage or pulses from high voltage pulse generator 340 are coupled across the first and second electrode arrays, it is believed that a plasma-like field is created surrounding first array electrode(s) 320A. This electric field ionizes the ambient air between the first and second electrode arrays and establishes an "OUT" airflow that moves in a downstream direction, towards the second array electrode(s) 330A. It is understood that the IN flow of ambient air can enter via vent(s) 250, that the electro-kinetically generated air flows in the direction of and at least partially through electrode(s) 330A, that the air flow is subjected to UV radiation 280, and exits device 200 as OUT, via one or more outlet vents 260. In the process, particulate matter (shown as x) entrained in the air flow can become electrostatically attached to the surface of electrode(s) 330A, as indicated in FIG. 2A.

It is believed that ozone and ions are generated simultaneously by the first array electrode(s) 320A, essentially as a function of the potential from generator 340 coupled to the first array. Ozone generation may be increased or decreased by increasing or decreasing the potential at the first array. Coupling an opposite polarity potential to the second array electrode(s) 330A essentially accelerates the motion of ions generated at the first array, producing the air flow denoted as "OUT" in the figures. As the ions move toward the second array, it is believed that they push or move air molecules toward the second array. The relative velocity of this motion may be increased by decreasing the potential at the second array relative to the potential at the first array.

For example, if +10 KV were applied to the first array electrode(s), and no potential were applied to the second array electrode(s), a cloud of ions (whose net charge is positive) would form adjacent the first electrode array. Further, the relatively high 10 KV potential would generate substantial local concentration of ozone. By coupling a relatively negative potential to the second array electrode(s), the velocity of the air mass moved by the net emitted ions increases, as momentum of the moving ions is conserved. This air movement dilutes the ozone concentration adjacent the first array electrodes, allowing the ozone concentration to be maintained at safe levels.

On the other hand, if it were desired to maintain the same effective outflow (OUT) velocity but to generate less ozone, the exemplary 10 KV potential could be divided between the electrode arrays. For example, generator 340 could provide +4 KV (or some other fraction) to the first array electrode(s) and −6 KV (or some other fraction) to the second array electrode(s). In this example, it is understood that the +4 KV and the −6 KV are measured relative to ground. Understandably it is desired that the present invention operate to output safe amounts of ozone. Accordingly, the high voltage is preferably fractionalized with about +4 KV applied to the first array electrode(s) and about −6 KV applied to the second array electrodes.

As noted, outflow (OUT) preferably includes safe amounts of $O_3$ that can destroy or at least substantially alter bacteria, germs, and other living (or quasi-living) matter subjected to the outflow. In preliminary experiments, it appears that subjecting the airstream to UV radiation 280 can somehow reduce the concentration of $O_3$ that is present in the OUT flow. Possibly the UV radiation hastens the disassociation of oxygen atoms comprising the ozone, but applicants have not thoroughly investigated this phenomenon. Understandably decreasing $O_3$ concentration, e.g., through use of UV lamp 290, can permit a higher velocity of OUT airflow, without necessarily increasing $O_3$ to undesirably high concentrations.

In the embodiment of FIG. 2A, device 200 has a cylindrical-shaped housing that is about 24" tall, and about 6" in cross-section or diameter. Input and output vents 250, 260 are preferably are each shaped as an annulus with an opening height of perhaps 0.5", although other configurations could be used. The housing preferably is made from a lightweight inexpensive material, ABS plastic for example. The lower surface of upper housing member 240 may be formed with a non-smooth finish or a non-light reflecting finish or color, to minimize a user 270 viewing reflected radiation 280 from lamp 290. As suggested by FIG. 2A, housing portion 240 preferably has a curved shape to direct the OUT airflow from a vertical orientation to an orientation that includes a horizontal component.

Ring-like electrode(s) 330A preferably have a cross-section or diameter of perhaps 2" to 4" and a length (upstream to downstream) of about 4" to 6". The electrode(s) may be formed from a cylinder or tube of metal, aluminum, stainless steel, etc. The pointed electrode(s) 320A are preferably made from a durable conductor such as tungsten, the better to withstand ionization effects. The length of the pointed portion of electrode(s) 320A is preferably at least 0.5", and the spaced-apart distance from the distal tip of electrode(s) 320A to the preferably curved or circular opening formed in electrode(s) 330A is about 1". Especially good electro-kinetic transport action can result when electrode(s) 320A are substantially coaxially and symmetrically disposed with respect to electrode(s) 330A. Thus, in FIG. 2A, the longitudinal axis of electrode(s) 320A and 331A are substantially coaxial.

Preferably operating parameters of the present invention are set during manufacture and are not user-adjustable. For example, increasing the peak-to-peak output voltage and/or duty cycle in the high voltage pulses generated by unit 340 can increase air flowrate, ion content, and ozone content. In the preferred embodiment, output flowrate is at least about 200 feet/minute, ion content is about 2,000,000/cc and ozone content is about 40 ppb (over ambient) to perhaps 2,000 ppb (over ambient). As described herein, decreasing the second electrode/first electrode radius of curvature R2/R1 ratio below about 20:1 will decrease flow rate, as will decreasing the peak-to-peak voltage and/or duty cycle of the high voltage pulses coupled between the first and second electrode arrays.

Within device 200, the electro-kinetically created airstream is subjected to sufficient radiation from lamp 290 for a sufficiently long time to substantially diminish if not destroy microorganisms that were present in the incoming ambient air. Thus, the output air (OUT) is conditioned in that particulate matter tends to precipitate electrostatically to the surface of electrode(s) 330A and be removed from the airflow, and microorganisms such as germs, fungi, bacteria, and viruses are substantially if not completely removed. Some ions are present in the output air, which can be beneficial, as are safe amounts of $O_3$. Occasionally it may be desirable to clean electrode(s) 330A so as to remove deposited particulate matter x from the electrode surface.

In the embodiment of FIG. 2B, electrical leads from lamp 290 to circuit 350 are omitted for ease of illustration, and lamp 290 is now shown disposed substantially coaxially with the electrode system 310 and with the airflow. It is understood that an advantage of coaxial lamp mounting is that essentially all of the radiated UV 280 may affect the airflow, whereas in the embodiment of FIG. 2A, some of the radiation must reflect from the interior wall surface of housing portion 230 before it can affect any portion of the airflow. If desired, multiple lamps 290 may be used, including at least one lamp mounted off-axis (e.g., FIG. 2A) and one lamp mounted coaxially (e.g., FIG. 2B).

Note too in FIG. 2B that the edges of electrode(s) 330A' facing upstream (e.g., towards electrode(s) 320A) have been chambered or rounded. Chambering is a preferred implementation of electrode(s) 330A in that beginning at the electrode regions facing electrode(s) 320A and continuing toward the opposite, downstream direction, a smooth and continuous second electrode array electrode surface is presented.

In the configuration of FIG. 2C, electrode(s) 320A are implemented using a portion of carbon or other material 320A' that terminates in a plurality of individual fibers, as shown. Various of the fibers act as individual pointed or pin-like electrodes. In the embodiment shown in FIG. 2C, the various fibers are essentially coaxially disposed with respect to ring-like electrodes 330A or 330A'.

FIG. 2D depicts a configuration in which ring-like electrode(s) are configured as 330A", a rather elongated cylindrical member with a smoothly outwardly flared edge in the upstream direction. In this configuration it can be advantageous to mount lamp 290 from one end. Again, for ease of illustration, electrical wires coupling lamp 290 to its power source have been omitted from the drawing. Note the inclusion of optional vanes 360, disposed within housing 210 so as to intentionally retard velocity of the airflow. These vanes can impart a vortex-like spin to the moving air, slowing the rate of flow, which increases the effective dwell time that UV radiation 280 from lamp 290 can act upon the airstream. It is understood that vanes 360 may also be included in the other configurations described, and to be described. In FIG. 2D, the diameter of electrode(s) 330A" may be 4" or so, and the length may be 12" or so, although other dimensions may be used. While FIG. 2D depicts electrode(s) 330A" as coupled to the positive port of high voltage pulse generator 340, it is understood that polarity of the pulses coupled to the first array and second array electrodes may in fact be reversed from what is shown.

FIG. 2E depicts a cascade configuration of first and second array electrodes that has been found to reduce audible hissing-like noise that can emanate from device 200. In this configuration, a pair of first array electrodes 320A, 320B are electrically series coupled to one port of high voltage generator 340, and a pair of second array electrodes 330A', 330B' are electrically series coupled to the other port of high voltage generator 340. The electrodes within a pair are preferably substantially symmetrically or coaxially disposed with respect to each other. Thus, electrode 320A is symmetrically and in this case also coaxially disposed with respect to electrode 330A', and electrode 320B is symmetrically and in this case also coaxially disposed with respect to electrode 330B'. Differently shaped ring-like electrodes 330A' and 330B' are depicted to suggest the relative freedom of design that exists. However in the various configurations, the R2/R1>10 ratio described earlier is preferably met.

Also shown in FIG. 2E is an optional ring (or other configuration) of moisture-retaining material 390, disposed adjacent at least one outlet port 260 as to present the least resistance to the outflow of air. In the preferred embodiment, moisture-retaining member 390 is a hollow collar-like cylinder, perhaps 0.125" thick of Porex™ UHMW X-4901 material, that can be moistened with water, with scent, perhaps with medication (e.g., asthma medication). Such material has a polyethylene base, exhibits a wicking action, and can absorb and retain substantial amounts of moisture. A user can periodically moisten this material, and the outflow of air (OUT) can contain not only beneficial amounts of ozone, some ions, relatively little particulate matter, and preferably little or no microorganisms, but may have increased humidity, if so desired by a user. Such material 390 may be included in the other configurations of the present invention described herein.

FIG. 2F depicts a configuration of the present invention in which housing 210 provides intake ports or vents 250 at an upper region and output ports or vents 260 at a lower region. In this configuration, germicidal UV lamp 290 is shown disposed in a lower region of the housing. Although FIG. 2F depicts a specific configuration of pin-like and ring-like electrodes, it is understood that other electrode configurations and/or additional electrode configurations could be used to establish a desired electro-kinetic airflow, to establish precipitation of particulate matter x in the incoming ambient air, to output ions, and to output safe amounts of ozone. Note that a collar or other configuration of moisture containing material 260 may optionally be provided.

Figures 3A, 3B:
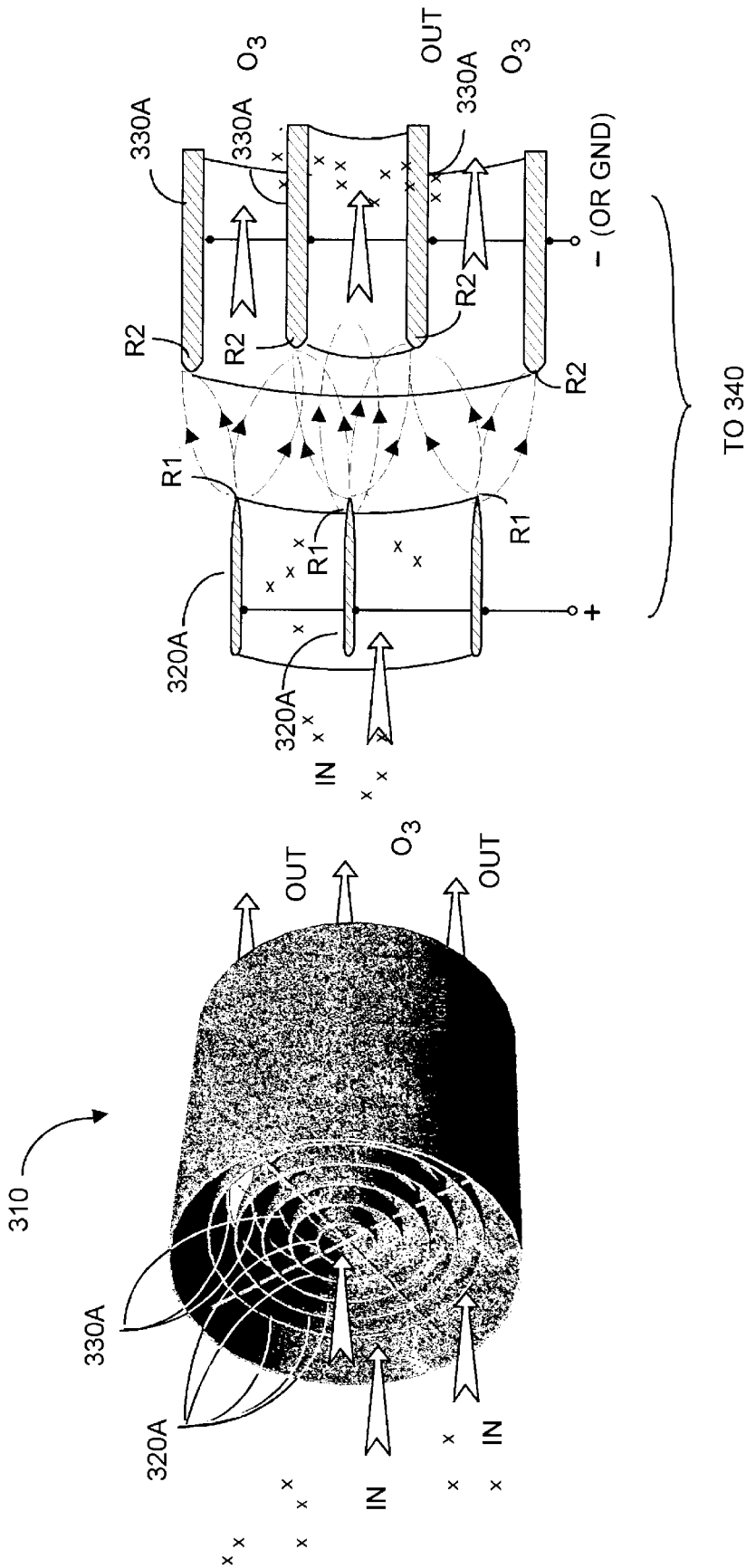
FIG. 3A is a view of an electrode system comprising concentric rings of first array electrodes and second array electrodes, according to the present invention.
FIG. 3B is a simplified cross-sectional side view of a portion of an electrode system such as shown in FIG. 3A, according to the present invention.

Turning now to FIGS. 3A and 3B, a compact configuration for an electrode system 310 is shown that can create the same total volume of air flow as can be generated from larger configuration electrode systems. The system is especially robust and can be removed from a device housing and cleaned of accumulated particulate particles and other matter, by being washed in an ordinary household dishwasher. FIG. 3B depicts force field lines resulting from application of high voltage from generator 340 across the electrode system.

In the configuration of FIG. 3A, a plurality of concentrically disposed first array electrodes 320A are disposed upstream from a plurality of concentrically disposed second array electrodes 330A. As best seen in FIG. 3B, the distal ends (the ends facing downstream or to the right in the figure) preferably are tapered or pointed or sharp. To depict the flexibility of design, the tapered distal end points of the first array electrodes 320A are shown essentially flush with each other in FIG. 3B, although they could instead be staggered. By contrast, the upstream facing preferably curved distal ends of second array electrodes 330A are shown staggered, although they could instead be flush with each other.

The first array electrodes 320A may be machined or otherwise formed from a durable metal, and are connected to each other electrically and to one output port of high voltage pulse generator 340, for example the positive port. The second array electrodes 330A similarly are formed from a durable metal and are connected to each other electrically and to the other end of the high voltage pulse generator 340. In this configuration as in the other electrode configurations, it is understood that one of the output ports or terminals of high voltage pulse generator 340 may in fact be at the same potential as ambient air.

The configuration shown in FIG. 3A may be perhaps 6" to 8" in outer diameter, perhaps 4" to 10" in length, with a spacing between adjacent concentric rings of elements 320A or of elements 330A of perhaps 0.25" to 0.5". Other dimensions may instead be used, however. If desired, the configuration of FIG. 3A may be slightly modified to use offset spiral configurations for electrodes 320A and for 330A.

Spiral configurations can simplify manufacturing as well as the electrically connections to the electrodes.

As shown in FIG. 3B, particulate matter (depicted as x) in the incoming air (IN) will tend to electrostatically adhere to the surface of the downstream second array electrodes 330A. The output airflow (OUT), however, will be relatively free of such particulate matter, and will contain ions and safe amounts of $O_3$. Further, the presence of a germicidal-type UV lamp 290 (not shown in FIGS. 3A, 3B) will ensure that microorganisms present in the incoming air will be substantially eliminated in the air outflow (OUT). It is further understood that, if desired, a ring or rings (or other configuration) of moisture retaining material 390 may be disposed, preferably adjacent a downstream portion of electrode assembly 310.

Figure 4B:
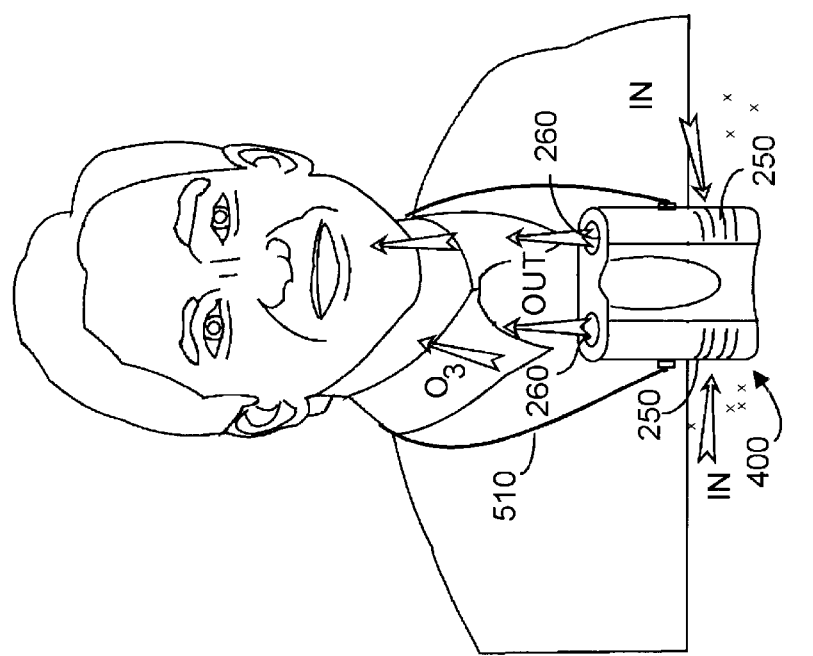
FIG. 4B depicts the device of FIG. 4A, worn around the neck of a user, according to the present invention.
Figure 4A:
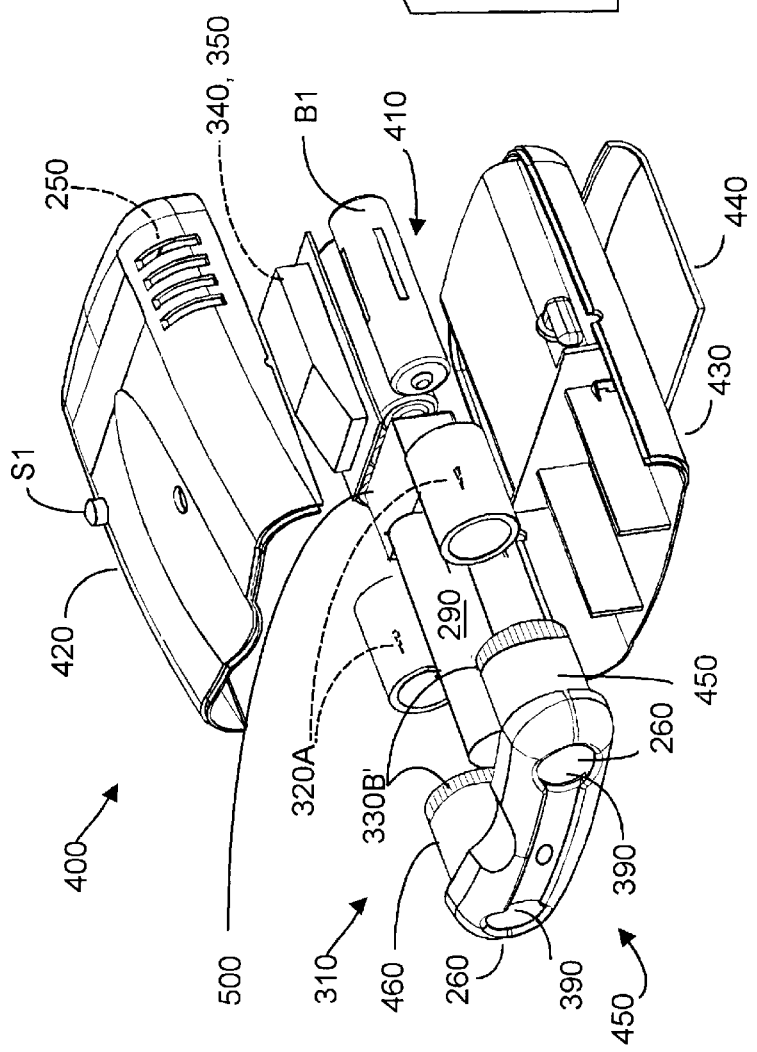
FIG. 4A is a breakaway view of a personal conditioner device that includes a germicidal lamp, a moisture-enhancing component, and an electro-kinetic air mover and/or an electric fan air mover, according to the present invention.

FIG. 4A is a perspective, breakaway view of a battery operable personal device 400, showing housing 410 as comprising an upper housing member 420 that includes intake vents 250, a lower housing member 430 and can house, among other components, batteries B1 to power device 400, and includes a battery hatch 440 to provide access to B1. An ON/OFF switch S1 can couple B1 to the high voltage generator and circuitry 340, 350 within housing 410. Housing 410 further includes a front housing portion 450 and provides outlet vents 260. In the preferred embodiment, the interior area of at least a portion of the outlet area includes foam like fluid-retaining material 260, as described above, which material, when wet, can augment humidity of th output airflow OUT.

In the embodiment shown, airflow preferably is electro-kinetically generated with an electrode system 310 that includes two pairs of electrode arrays. Alternatively, or in addition, a small DC-powered fan 500 may be included to create an airflow, albeit without generating ozone and/or ions. In FIGS. 4A, pin-like and ring-like electrodes 320A and 330B'. First array electrodes 320A may be as shown in FIGS. 2A–2F, and second array electrodes 330B' preferably are flared, as shown in FIG. 2E. Each pin-like or pointed electrode 320A is upstream and preferably coaxial from a ring-like electrode 330B'. A collar of moisture retaining material 390 is disposed within housing portion 450 so as to be subjected to the airflow passing through the smooth and continuous interior surface of an adjacent electrode 330B'.

Device 400 further includes a germicidal type UV lamp 290, such as described earlier herein. Lamp 290 is disposed within housing 410 so that the airflow (whether created electro-kinetically or by fan 500) is subjected to UV radiation from the lamp.

FIG. 4B shows device 400 suspended from the neck of a user by a cord 510. The battery operated device 400 lends itself to use in crowded areas such as motor vehicles, airplanes, etc. where the ambient air might be less than pristine. The inclusion of lamp 290 within device 400 will promote the destruction of germs, bacteria, fungi, viruses in the output airflow (OUT). The electro-kinetic generation of the airflow promotes silent operation of device 400, serves to output air that has been at least partially cleaned of particulate matter, and that can include ions and/or ozone. Further, the inclusion of wettable material 390 allows the wearer or user of device 400 to augment moisture in the outflow of air, and/or to add scented liquid and/or medication to further augment the nature and quality of the output airflow. Although device 400 is shown worn around a user's body in FIG. 4B, device 400 may also be placed on an automobile dashboard and, if desired, powered from the vehicle battery.

Modifications and variations may be made to the disclosed embodiments without departing from the subject and spirit of the invention as defined by the following claims.

What is claimed is:

1. An air transporter-conditioner comprising:

a housing defining at least one input port and one output port, and an air channel therebetween;

a germicidal ultraviolet lamp, disposed in said housing, to emit radiation upon being energized;

wherein said housing is configured to preclude human viewing of radiation emitted directly from said lamp when said lamp is energized;

an electro-kinetic system, disposed in said housing, to create an airflow moving from said input port downstream to said output port, and to subject at least a portion of said airflow to at least a portion of radiation emitted by said lamp;

said electro-kinetic system including a first electrode array having at least one electrically conductive electrode with a distal effective radius R1, and spaced-apart therefrom in a downstream direction therefrom a second electrode array having at least one electrically conductive electrode with a distal effective radius R2, where R2≧10R1, and further including a high voltage system configured to output pulses of duty cycle from about 10% to about 100% and being at least 5 KV magnitude peak-to-peak, said high voltage system coupled between said first electrode array and said second electrode array;

wherein relative to air entering said input port, air exiting said output port of said air-transporter conditioner has at least one of (a) reduced levels of microorganisms, (b) reduced amount of particulate matter, (c) ions, and (d) ozone.

2. The air transporter-conditioner of claim 1, further including a material able to retain liquid disposed in said housing to augment said airflow with at least one of (a) humidity, (b) scent, and (c) medicinal content.

3. The air transporter-conditioner of claim 1, wherein at least one electrode in said first electrode array has a tapered profile.

4. The air transporter-conditioner of claim 1, wherein at least one electrode in said first electrode array is pointed.

5. The air transporter-conditioner of claim 1, wherein at least one electrode in said first electrode array has a distal end comprising electrically conductive fibers.

6. The air transporter-conditioner of claim 1, wherein at least one electrode in said second electrode array defines an opening through which at least a portion of said airflow may pass, and further has a smooth and continuous surface surrounding airflow passing through said second electrode array.

7. The air transporter-conditioner of claim 1, wherein at least one electrode in said second electrode array defines a circular opening through which at least a portion of said airflow may pass, and is disposed symmetrically downstream from an electrode in said first electrode array.

8. The air transporter-conditioner of claim 1, wherein said first electrode array includes at least two concentric elements that each define a tapered cross-section in a downstream direction.

9. The air transporter-conditioner of claim 1, wherein said second electrode array includes at least two concentric elements that each define a rounded cross-section in an upstream direction.

10. The air transporter-conditioner of claim 1, wherein:
said first electrode array includes at least two concentric elements that each define a tapered cross-section in a downstream direction;
said second electrode array includes at least two concentric elements that each define a rounded cross-section in an upstream direction;
wherein an adjacent-most electrode in said first electrode array is symmetrically disposed relative to a pair of adjacent-most electrodes in said second electrode array.

11. The air transporter-conditioner of claim 10, wherein said first electrode array and said second electrode array comprise a single cylindrically-shaped electrode system.

12. The air transporter-conditioner of claim 11, wherein at least two electrodes in said second electrode array are staggered in distance relative to an adjacent-most electrode in said first electrode array.

13. An air transporter-conditioner, comprising;
a housing having an inlet and an outlet;
an ion generator configured to create an airflow between the inlet and the outlet, the generator having a first group of electrodes, a second group of electrodes, and a high voltage generator coupled between the first and second group of electrodes; and
a germicidal lamp configured to expose the airflow to germicidal light to reduce microorganisms within the airflow, the lamp disposed within the housing so that the lamp is not viewable by an individual.

14. The air transporter-conditioner as recited in claim 13, wherein the first group of electrodes includes at least one electrode with a characteristic selected from the group consisting of (i) a tapered pin-shaped electrode that terminates in a pointed tip, (ii) a tapered pin-shaped electrode that terminates in a plurality of individual fibers, and (iii) a plurality of concentric circles.

15. The air transporter-conditioner as recited in claim 13, wherein the second group of electrodes includes at least one electrode with a characteristic selected from the group consisting of (i) an elongated cylindrical tube, and (ii) a plurality of concentric circles.

16. The air transporter-conditioner as recited in claim 13, wherein the second group of electrodes is downstream of the first group of electrodes.

17. The air transporter-conditioner as recited in claim 13, further including a moisture retaining element to place into the airflow at least one of the following characteristics selected from the group consisting of (i) humidity, (ii) scent, and (iii) medicinal content.

18. The air transporter-conditioner as recited in claim 13, wherein the housing further has vanes to slow down the velocity of the airflow as it passes the germicidal lamp, exposing the airflow to the germicidal light for an increased period of time.

19. The air transporter-conditioner as recited in claim 13, wherein the internal surface of the housing is diffused to minimize deflection of the ultraviolet light emitted from the germicidal lamp, and further to minimize the static charge build up.

20. The air transporter-conditioner as recited in claim 13, wherein the germicidal lamp is a type UV-C lamp that preferably emits ultraviolet radiation having a wave length of approximately 254 nm.

21. The air transporter-conditioner as recited in claim 13, wherein the longitudinal axis of the germicidal lamp is parallel to the airflow to maximize the length of time the microorganisms are subjected to the radiation emitted by the germicidal lamp.

22. An air transporter-conditioner, comprising
a housing having an inlet and an outlet;
means for creating an airflow between the inlet and the outlet, and further for generating ionized air and ozone;
means for reducing microorganisms in the airflow; and
means for placing into the airflow at least one of the following characteristics selected from the group consisting of (i) humidity, (ii) scent, and (iii) medicinal content.

23. An air transporter-conditioner as recited in claim 22, wherein the means for creating an airflow includes an ion generator having a first group of electrodes and a second group of electrodes, and further including a high voltage generator coupled between the first and second group of electrodes.

24. An air transporter-conditioner as recited in claim 23, wherein the first group of electrodes includes at least one electrode with a characteristic selected from the group consisting of (i) a tapered pin-shaped electrode that terminates in a pointed tip, (ii) a tapered pin shaped electrode that terminates in a plurality of individual fibers, and (iii) a plurality of concentric circles.

25. An air transporter-conditioner as recited in claim 23, wherein the second group of electrodes includes at least one electrode with a characteristic selected from the group consisting of (i) an elongated cylindrical tube, and (ii) a plurality of concentric circles.

26. An air transporter-conditioner as recited in claim 23, wherein the second group of electrodes is downstream of the first group of electrodes.

27. An air transporter-conditioner as recited in claim 22, wherein the means for reducing microorganism is a germicidal lamp exposing the airflow to germicidal light.

28. An air transporter-conditioner as recited in claim 27, wherein the longitudinal axis of the germicidal lamp is parallel to the airflow to maximize the length of time the microorganisms are subjected to the radiation emitted by the germicidal lamp.

29. An air transporter-conditioner, comprising;
a housing having an inlet and an outlet;
an ion generator configured to create an airflow between the inlet and the outlet; and
a germicidal lamp upstream of said ion generator configured to expose the airflow to germicidal light to reduce microorganisms within the airflow.

30. An air transporter-conditioner, comprising;
a housing having an inlet and an outlet;
an ion generator configured to create an airflow between the inlet and the outlet; and
a germicidal lamp configured to expose the airflow to germicidal light to reduce microorganisms within the airflow, the lamp disposed within the housing so that the lamp is not viewable by an individual.

31. An air transporter-conditioner, comprising;
a housing having an inlet and an outlet;
an ion generator configured to create an airflow between the inlet and the outlet; and
a germicidal device upstream of said ion generator configured to reduce microorganisms within the airflow.

32. An air transporter-conditioner, comprising;
a housing having an inlet and an outlet;
an ion generator configured to create an airflow between the inlet and the outlet; and
a germicidal device configured to reduce microorganisms within the airflow, the device disposed within the housing so that the device is not directed at said ion generator.

33. An air transporter-conditioner, comprising a housing having an inlet and an outlet;

means for creating an airflow between the inlet and the outlet, and further for generating ionized air; and means for reducing microorganisms in the airflow located upstream of said airflow creating means.

34. An air transporter-conditioner, comprising a housing having an inlet and an outlet;

means for creating an airflow between the inlet and the outlet, and further for generating ionized air; and means for reducing microorganisms in the airflow, which microorganism reducing means is dispensed within said housing;

wherein said housing is configured to preclude human viewing of said means for reducing microorganisms.

35. An air transporter-conditioner, comprising a housing having an inlet and an outlet;

means for creating an airflow between the inlet and the outlet, and further for generating ionized air and ozone; and means for reducing microorganisms in the airflow, which reducing means is not directed at said creating means.

36. An air transporter-conditioner comprising:

a housing defining at least one input port and one output port, and an air channel therebetween;

a germicidal ultraviolet lamp, disposed in said housing, to emit radiation upon being energized;

wherein said housing is configured to preclude human viewing said lamp when said lamp is energized;

an electro-kinetic system, disposed in said housing, to create an airflow moving from said input port downstream to said output port, and to subject at least a portion of said airflow to at least a portion of radiation emitted by said lamp;

said electro-kinetic system including a first electrode array having at least one electrically conductive electrode with a distal effective radius R1, and spaced-apart therefrom in a downstream direction therefrom a second electrode array having at least one electrically conductive electrode with a distal effective radius R2, where $R2 \geq 10R1$, and further including a high voltage system configured to output pulses of duty cycle from about 10% to about 100% and being at least 5 KV magnitude peak-to-peak, said high voltage system coupled between said first electrode array and said second electrode array;

wherein relative to air entering said input port, air exiting said output port of said air-transporter conditioner has at least one of (a) reduced levels of microorganisms, (b) reduced amount of particulate matter, (c) ions, and (d) ozone.

37. An air transporter-conditioner comprising:

a housing defining at least one input port and one output port, and an air channel therebetween;

a germicidal ultraviolet lamp, disposed in said housing, to emit radiation upon being energized;

wherein said housing is configured to preclude human viewing said lamp;

an electro-kinetic system, disposed in said housing, to create an airflow moving from said input port downstream to said output port, and to subject at least a portion of said airflow to at least a portion of radiation emitted by said lamp;

said electro-kinetic system including a first electrode array having at least one electrically conductive electrode with a distal effective radius R1, and spaced-apart therefrom in a downstream direction therefrom a second electrode array having at least one electrically conductive electrode with a distal effective radius R2, where $R2 \geq 10R1$, and further including a high voltage system configured to output pulses of duty cycle from about 10% to about 100% and being at least 5 KV magnitude peak-to-peak, said high voltage system coupled between said first electrode array and said second electrode array;

wherein relative to air entering said input port, air exiting said output port of said air-transporter conditioner has at least one of (a) reduced levels of microorganisms, (b) reduced amount of particulate matter, (c) ions, and (d) ozone.

* * * * *